United States Patent [19]

Matthews

[11] Patent Number: 4,576,962

[45] Date of Patent: Mar. 18, 1986

[54] PROSTAGLANDIN ANALOGUES

[75] Inventor: Randall S. Matthews, Cincinnati, Ohio

[73] Assignee: The Procter & Gamble Company, Cincinnati, Ohio

[21] Appl. No.: 607,351

[22] Filed: May 4, 1984

Related U.S. Application Data

[63] Continuation-in-part of Ser. No. 542,210, Oct. 19, 1983, abandoned, which is a continuation-in-part of Ser. No. 439,504, Nov. 5, 1982, abandoned.

[51] Int. Cl.$^4$ .................. C07C 177/00; A61K 31/557
[52] U.S. Cl. ..................................... 514/530; 514/573; 514/690; 549/465; 560/119; 560/121; 562/501; 562/503; 568/374; 568/379
[58] Field of Search .................. 560/121; 562/503; 514/530, 573, 690; 568/379

[56] References Cited

U.S. PATENT DOCUMENTS

| | | | |
|---|---|---|---|
| 3,984,400 | 10/1976 | Eggler | 260/240 |
| 4,029,681 | 6/1977 | Smith . | |
| 4,198,430 | 4/1980 | Gandolfi et al. . | |
| 4,230,721 | 10/1980 | Gandolfi et al. | 424/285 |
| 4,242,508 | 12/1980 | Gandolfi et al. | 542/430 |
| 4,250,188 | 2/1981 | Gandolfi et al. | 424/285 |
| 4,254,137 | 3/1981 | Gandolfi et al. | 424/283 |
| 4,259,244 | 3/1981 | Gandolfi et al. | 260/346.22 |
| 4,262,016 | 4/1981 | Gandolfi et al. | 424/283 |
| 4,271,183 | 6/1981 | Gandolfi et al. | 424/285 |
| 4,271,184 | 6/1981 | Gandolfi et al. | 424/285 |
| 4,277,491 | 7/1981 | Gandolfi et al. | 424/285 |
| 4,288,617 | 9/1981 | Sih . | |
| 4,289,899 | 9/1981 | Sih . | |
| 4,292,442 | 9/1981 | Sih . | |
| 4,297,368 | 10/1981 | Gandolfi et al. | 424/285 |
| 4,303,670 | 12/1981 | Gandolfi et al. | 424/285 |
| 4,328,240 | 5/1982 | Gandolfi et al. | 424/285 |
| 4,345,984 | 8/1982 | Mihelich . | |

FOREIGN PATENT DOCUMENTS

| | | |
|---|---|---|
| 520037 | 4/1980 | Australia . |
| 9869 | 4/1980 | European Pat. Off. . |
| 2376147 | 7/1978 | France . |
| 7810862 | 5/1980 | Netherlands . |

OTHER PUBLICATIONS

F. F. Sun et al., "Advances in Prostaglandin and Thromboxane Research," vol. 1, p. 163 (1976), Samuelson & Bouletti, Ed., Raven Press, NY.

Gandolfi et al., "Advances in Prostaglandin and Thromboxane Research," vol. 1, p. 209 (1976), Samuelson & Bouletti, Ed., Raven Press, NY.

Epolitti et al., *Gastroenterology*, 80, pp. 55-59 (1981).

*Primary Examiner*—Robert Gerstl
*Attorney, Agent, or Firm*—Richard C. Witte; Jack D. Schaeffer; Steven J. Goldstein

[57] ABSTRACT

The 13,14-didehydro-15-oxo analogues of natural prostaglandins possess high cytoprotective activity and low diarrheogenic activity, low anti-hemostatic activity and low smooth muscle contraction activity.

32 Claims, No Drawings

PROSTAGLANDIN ANALOGUES

CROSS REFERENCE TO RELATED APPLICATIONS

This application is a continuation-in-part of prior application Ser. No. 542,210, filed Oct. 19, 1983, which is a continuation-in-part of application Ser. No. 439,504, filed Nov. 5, 1982, both abandoned.

TECHNICAL FIELD

This invention relates to novel prostaglandin analogues which are useful in treating and preventing gastric inflammatory diseases in humans and lower animals.

Certain prostaglandins and prostaglandin analogues are known to be effective in the treatment or prevention of gastric ulcers. In particular, $PGE_2$ is known to have cytoprotective anti-ulcer properties. However, $PGE_2$ suffers from a serious stability problem in that it is readily metabolized. The hydroxy group at the $C_{15}$ position is subject to rapid dehydrogenation to the corresponding ketone, which is significantly less active or probably not active at all. Attempts have been made to increase the stability of $PGE_2$ by substituting methyl groups at the $C_{15}$ and $C_{16}$ positions. The better stability of 15(R)-15-methyl $PGE_2$ and 16,16-dimethyl $PGE_2$ results in a lower value of the $ED_{50}$ (for cytoprotection in a rat model) of these compounds as compared to the natural prostaglandin $PGE_2$.

Prostaglandins and their analogues possess serious side effects which vastly reduce their utility as anti-ulcer drugs. In particular, the diarrheogenic effect of prostaglandins, their inhibitory effects on human platelet aggregation and their effect on smooth muscle contraction pose serious problems when these compounds are used as anti-ulcer drugs. There is therefore a continuing need for cytoprotective prostaglandin analogues which have a low diarrheogenic activity, a low anti-hemostatic activity, and low smooth muscle contraction activity.

It is therefore an object of this invention to provide prostaglandin analogues which are not subject to inactivation by dehydrogenation at the $C_{15}$ position. It is a further object of this invention to provide prostaglandin analogues which exhibit cytoprotective activity combined with low diarrheogenic activity, a low anti-hemostatic activity and low smooth muscle contraction activity. Another object of this invention is to provide novel pharmaceutical compositions for treating or preventing gastric inflammatory diseases. A method of treating or preventing gastric inflammatory diseases is also an object of this invention.

BACKGROUND ART

It is well documented that metabolic deactivation of prostaglandins involves the dehydrogenation of the secondary alcohol at the $C_{15}$ position. See, for example, F. F. Sun et al., "Advances in Prostaglandin and Thromboxane Research," Vol. 1, p. 163 (1976), Samuelson & Bouletti, Ed., Raven Press, New York; see also Gandolfi et al., "Advances in Prostaglandin and Thromboxane Research," Vol. 1, p. 209 (1976), Samuelson & Bouletti, Ed., Raven Press, New York; Epolitti et al., Gastroenterology, 80, pp. 55-59 (1981).

Parenterally administered prostaglandins and prostaglandin analogues are subject to dehydrogenation at the $C_{15}$ position due to prostaglandin 15 hydroxy dehydrogenase (PGDH). When given orally, these compounds are subject to intragastric dehydrogenation at their $C_{15}$ position. Epolitti et al., cited above, report that 15(S),15-methyl $PGE_2$ and 16,16-dimethyl $PGE_2$ are more stable than $PGE_2$ itself.

Gandolfi et al., cited above, disclose that 16(S),16-methyl-13-dehydro $PGE_2$ and its isomer, 16(R),16-methyl-13-dehydro $PGE_2$ possess potent gastric anti-ulcer properties and are not substrates for the enzyme PGDH. It is not disclosed whether these compounds would also possess improved intragastric stability. A $C_{13}$–$C_{14}$ triple bond in 16-methyl or 16,16-dimethyl $PGF_2$ results in fairly weak reactive compounds.

It is well established in the art that metabolic oxidation of the secondary alcohol at the $C_{15}$ position results in a loss of activity. Introduction of methyl groups at the $C_{15}$ and $C_{16}$ positions results in a better stability against PGDH and against intragastric oxidation. Introduction of a $C_{13}$–$C_{14}$ triple bond might result in increased stability against PGDH. It is not known whether it also results in increased intragastric stability. Moreover, introduction of a $C_{13}$–$C_{14}$ triple bond may result in important loss of activity.

SUMMARY OF THE INVENTION

The 13,14-didehydro-15-oxo analogues of the prostaglandins $PGE_1$, $PGE_2$, $PGF_{2\alpha}$ and $PGI_2$ and pharmaceurically acceptable salts and esters thereof have been found to possess an unexpectedly high cytoprotective activity. Since these compounds further possess low diarrheogenic activity, low anti-hemostatic activity and low smooth muscle contraction activity, these compounds are extremely suitable for use in the treatment and prophylaxis of gastric inflammatory diseases.

DETAILED DESCRIPTION OF THE INVENTION

By "prostaglandin" or "natural prostaglandin" herein is meant any naturally occurring compound derived from arachidonic acid and characterized by a five-membered ring structure. An overview of these compounds is found in Nelson et al., "Prostaglandins and the Arachidonic Acid Cascade," C&EN, Aug. 16, 1982, pp. 30-44, incorporated herein by reference.

By "prostaglandin analogue" herein is meant any compound which has the basic structure of one of the natural prostaglandins, having a five-membered ring and at least 16 carbon atoms, but which does not itself occur in nature.

By "pharmaceutically acceptable salts and esters" as used herein is meant esters and salts of the prostaglandin analogues which have the same general pharmacological properties as the acid form from which they are derived, and which are acceptable from a toxicity viewpoint.

Specifically included in this term are salts and esters of the type disclosed in U.S. Pat. No. 4,029,681, issued June 19, 1977 to Smith, and in U.S. Pat. No. 4,288,616, issued Sept. 8, 1981, the disclosures of which are incorporated herein by reference. Preferred esters are $C_1$–$C_{12}$ alkyl esters, particularly methyl and ethyl. Preferred salts are the alkali metal salts, in particular sodium and potassium, ammonium, and amine salts, in particular tris(hydroxymethyl)aminomethane salt.

By "gastric inflammatory disease" as used herein is meant gastric ulceration and other types of gastro-intestinal damage or discomfort, including but not limited to those types caused by chronic hyperchlorhydria, by gastro-intestinal surgery, by shock or trauma, by use and abuse of drugs or alcohol, and the like.

By "person at risk", or "person in need of such treatment", as used herein, is meant any individual who suffers a significant risk of ulceration, or other gastro-intestinal damage or discomfort, if left untreated, or if the acid levels of the gut remain uncontrolled. For example, those whose gastro-intestinal mucosa has already been compromised or ulcerated; those who have been diagnosed as suffering from chronic hyperchlorhydria; those suffering from peptic ulcer disease and its complications, such as hemorrhage or penetration; those who have been diagnosed as having a pathology which in turn causes hyperchlorhydria, such as Zollinger-Ellison Syndrome and related diseases; those who have or will shortly undergo gastro-intestinal surgery, i.e., pre- and post-operative gastro-intestinal surgical patients; those suffering from shock or trauma; those undergoing other treatment regimens which can cause hypochlorhydria or gastric inflammatory disease except non-steroidal anti-inflammatory agents; those who have had recent acute exposure to a cytodestructive agent, such as ionizing electromagnetic or particular radiation; those who have had acute or chronic gastro-intestinal exposure, for example, by ingestion, of noxious gastric cytodestructive or cytotoxic chemical agents; or those who are diagnosed as being exposed to a stressful environment regardless of origin, especially those exposed to this environment who have demonstrated recurrent gastritis or ulcer disease when exposed to such an environment.

This invention relates to a novel class of prostaglandin analogues; members of this class all possess a triple bond at the $C_{13}$–$C_{14}$ position, and an oxo-substituent at the $C_{15}$ position. The compounds therefore basically are the 13,14-didehydro-15-oxo analogues of natural prostaglandins, but may differ further from the natural prostaglandins in that they lack the hydroxyl group at the 11-position and/or contain e.g. substituents at the 16-position, the 19-position or the 20-position, a double bond in the carboxylic acid side chain, etc.

The 13,14-didehydro-15-oxo-prostaglandin analogues of this invention have the general formula

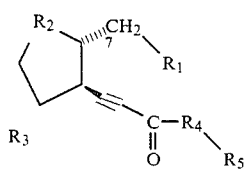

wherein $R_1$ is

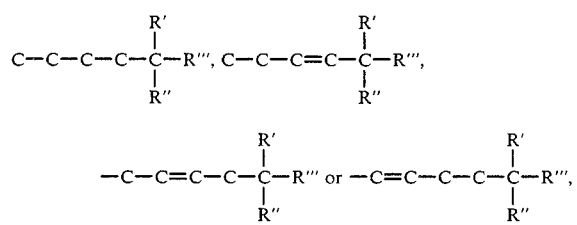

wherein

R' and R'' are each independently H, $CH_3$, $C_2H_5$ or $C_3H_7$ and R''' is $CH_2OH$, or $COOR_6$, wherein $R_6$ is hydrogen or a pharmaceutically acceptable salt or ester;

$R_2$ is

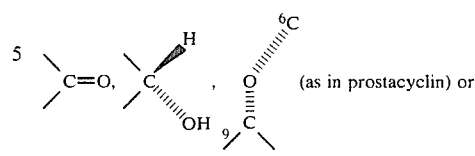 (as in prostacyclin) or

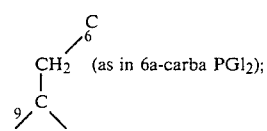 (as in 6a-carba $PGI_2$);

$R_3$ is hydrogen, hydroxyl, hydroxymethyl, methylene, or R''''—O—, wherein R'''' is an alkyl having from 1 to 4 carbon atoms;

$R_4$ is

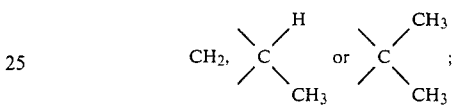

and $R_5$ is $C_2H_5$, $C_3H_7$, $C_4H_9$ or $C_5H_{11}$.

These compounds will hereinafter be referred to as "the prostaglandin analogues of the present invention."

Preferred compounds within this class are those in which $R_4$ is $CH_2$; $R_5$ is $C_4H_9$; $R_3$ is hydrogen; $R_2$ is $>C=O$; or $R_1$ is $C_5H_{10}COOH$ or $—C=C—C_3H_6COOH$, and compounds comprising two or more of these preferred substituents combined.

Specifically preferred compounds are the prostaglandin analogues of the formula:

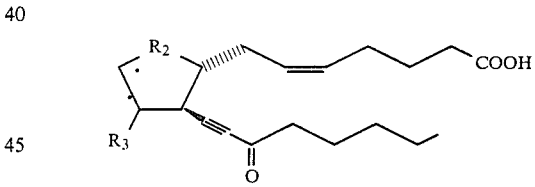

wherein $R_2$ is

\>C=O or \>C{H, OH};

and $R_3$ is hydrogen, hydroxyl, or hydroxymethyl; and pharmaceutically acceptable salts and esters thereof; and those of the formula

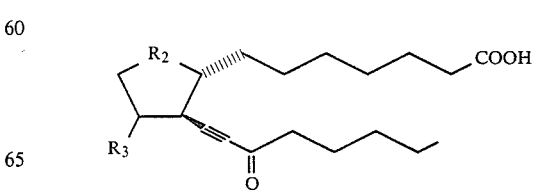

wherein $R_2$ is

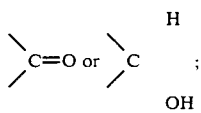

$R_3$ is hydrogen, hydroxyl or hydroxymethyl; and pharmaceutically acceptable salts and esters thereof.

Specific examples of the prostaglandin analogues of the present invention are the 13,14-didehydro-15-oxo analogue of $PGF_2$; the 13,14-didehydro-15-oxo analogue of $PGE_2$; the 13,14-didehydro-15-oxo analogue of $PGE_1$; the 11-deoxy-13,14-didehydro-15-oxo analogue of $PGF_2$; the 11-deoxy-13,14-didehydro-15-oxo analogue of $PGE_2$; the 11-deoxy-13,14-didehydro-15-oxo analogue of $PGE_1$; and the 6a-carba-13,14-didehydro-15-oxo analogue of $PGI_2$.

EXAMPLE I

The prostaglandin analogues of the present invention may be prepared from commercially available starting materials. In order to exemplify how the compounds of the present invention are synthesized the reaction scheme for the preparation of 11-deoxy-13,14-didehydro-15-oxo $PGE_1$ is as follows:

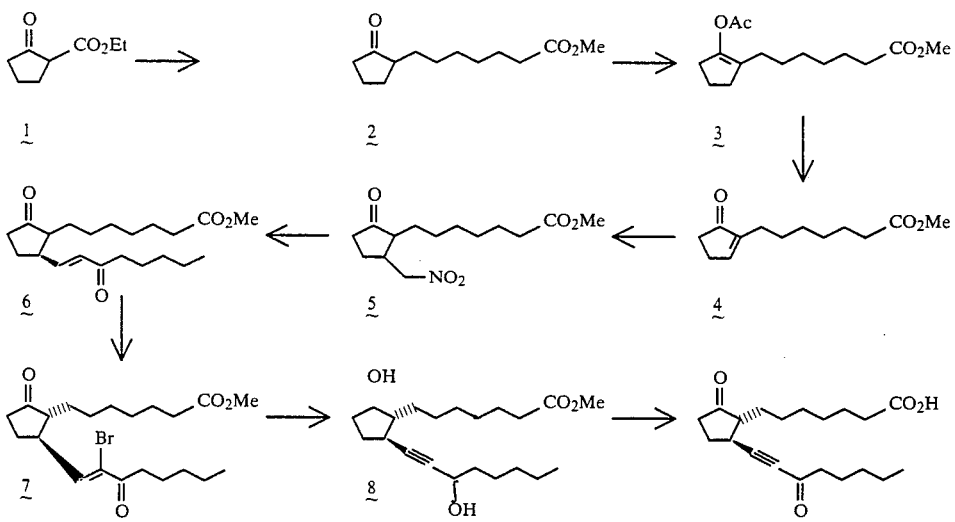

Methyl 2-oxocyclopentane carboxylate 1 can be converted to enone 4 as described by Bernady et al., *J. Org. Chem.* 45, 4702 (1980) and by Novah et al., *Synthesis* 1974, 353. A one-step synthesis of 4 from 2 is described by Miller, et al., *Tetrahedron Lett.* 1983, 555, incorporated herein by reference. The conversion of enone 4 to the diketone 6 is described by Bagli et al., *Tetrahedron Lett.*, 1972, 3815. The cited articles are incorporated herein by reference. The conversion of 6 to 8 is similar to reactions disclosed in U.S. Pat. No. 4,629,681, issued June 14, 1977 to Smith, incorporated herein by reference.

A. Keto-ester 2

A stirred solution of ethyl 7-bromo-heptanoate (38.76 g, 0.16 mol), ethyl 2-oxo-cyclopentane carboxylate (25.54 g, 0.16 mol), and anhydrous potassium carbonate (44.96 g) in dry acetone (330 mL) was refluxed overnight. The mixture was then cooled and filtered, and the filter cake was washed with several portions of acetone. The acetone portions were combined and concentrated in vacuo. To the resulting residue was then added water (200 mL) and conc. sulfuric acid (100 mL). The solution was refluxed overnight. After cooling to rt, the reaction mixture was extracted with ether (2×200 mL). The combined ether extracts were washed with water (400 mL), dried, filtered, and concentrated in vacuo to give the carboxylic acid, as a brown oil. That material was dissolved in methanol (600 mL) and conc. sulfuric acid (0.5 mL) was added; the mixture was then heated at reflux overnight. After concentration in vacuo to remove most of the methanol, the reaction mixture was transferred to a separatory funnel with ether (250 mL) and washed sequentially with water and saturated sodium bicarbonate. The ether layer was dried, filtered, and concentrated in vacuo to give the crude ester, which was purified by fractional distillation (collected fraction with bp=105°–115° C. at 0.1–0.2 mm) to yield pure ester 2 (22.44 g, 61% yield). The product was judged to be pure by vpc and NMR (C-13 NMR at 22.5 MHz: 221.0, 173.9, 51.2, 48.9, 37.9, 33.8, 29.4 (2C), 29.0, 28.8, 27.2, 24.7, 20.6 ppm). This reaction was also run on a 0.295 mole scale following the procedure above; the yield was slightly lower (54%).

B. Enone acetate 3

A mixture of keto-ester 2 (22.44 g, 0.993 mol), acetic anhydride (45 mL), and p-toluenesulfonic acid (0.2 g) was placed in a flask fitted with a short column topped with a small distillation head, and heated at such a rate that the acetic acid formed in the reaction slowly distilled off. After about 10 hr, the temperature of the distilling liquid had reached 200° C., indicating that acetic anhydride was coming over. The reaction mixture was then cooled to rt and added dropwise to a 1 L Erlenmeyer flask containing 200 mL of 1N sodium bicarbonate. The resulting mixture was extracted with hexane (3×150 mL), and the combined hexane layers were dried, filtered, and concentrated in vacuo. The crude product was purified by fractional distillation (collected fraction bp 115°–120° C. at 0.2 mm) to give pure enol acetate 3 (21.09 g, 79% yield). $^1$H NMR at 60 MHz: 3.6 (s, 3H), 2.1 (s,3H).

C. Enone 4

To a mixture of calcium carbonate (8.12 g) in 78 mL of water, stirred at 0° C., was simultaneously added a solution of enol acetate 3 (21 g, 78.69 mmol) in 10 mL of chloroform and a solution of bromine (4.21 mL) in 12.3 mL of carbon tetrachloride. The addition took ca 10 minutes; at that time a small, additional amount of bromine was added so that the red color remained, indicating a slight excess of bromine. After stirring at 0° C. for 20 min, the reaction mixture was transferred to a separatory funnel; the layers were separated, and the aqueous portion was extracted with chloroform. The combined chloroform layers were washed with 10% sodium bisulfate, dried, filtered, and concentrated in vacuo (the temperature on the rotovap should be 30°-35° C. to avoid decomposing the sensitive bromo-ketone, which should be used in the next step immediately upon concentration). A mixture of lithium bromide (14.35 g), lithium carbonate (13.72 g), and DMF (104 mL) was rotovaped three times with benzene (to remove water), and then set up to reflux. To that refluxing mixture was added the bromo-ester from above. After 30 min the reaction mixture was cooled to rt and poured into a 2 L Erlenmeyer. Aqueous, 1N HCl was added slowly, with stirring, until the mixture tested acidic on pH paper; it was then extracted with ether (300 mL, 600 mL, 600 mL). The combined ether layers were dried, filtered, and rotovaped to give crude 4. This reaction was repeated on a 42.18 g scale, and the combined, crude product from the two runs was purified by short path distillation (bp 163° C. at 0.1-0.2 mm) to give 27.4 g (52% yield) enone 4: NMR (60 MHz) 7.2 (m,1H), 3.6 (s,3H). The enone thus isolated was ca 80-90% pure; it may be purified by chromatography, but it was normally used in the next reaction without further purification.

D. Nitro-ketone 5

A dried flask was charged with enone 4 (29.5 g, 131 mmol, crude, distilled product from the preceding reaction) and dry methanol (249 mL). Nitromethane (33.6 mL) was added, followed by sodium methoxide (124.2 mL of a 1.06N solution in methanol). The reaction was stirred at rt overnight. The reaction mixture was then added to 500 mL of 0.1N HCl and was extracted with methylene chloride (3×500 mL). The combined organic layer was filtered and concentrated in vacuo to give the crude product, which was chromatographed on 1 kg of silica gel (mplc) with 3:1 hexane/EtOAc to give 23.446 g pure 5 (62% yield): $^1$H NMR (60 MHz) 4.5 (m, 2H), 3.6 (s,3H).

E. Diketo-olefin 6

To a stirred solution of nitro-ketone 5 (8.5 g, 298 mmol) in 84 mL of dry methanol, under argon at rt, was added 42.2 mL of a 1.06N solution of sodium methoxide in methanol, via syringe. The mixture was stirred for 10 min. A beaker containing 1080 mL of 1:8 conc sulfuric acid/water was cooled to 0° C. with stirring, and the reaction mixture from above was added dropwise via pipette. After 5 min the resulting solution was extracted with methylene chloride (2×300 mL); the combined extracts were filtered and concentrated in vacuo to give ca 7 g crude aldehyde, used without purification in the next step.

To a stirred solution of dimethyl (2-oxoheptyl)phosphonate (6.3 mL, 1.1 equiv) in dry THF (310 mL), at 0° C. under argon, was added n-butyllithium (17.5 mL of a 1.65M solution in hexane, 1.05 equiv) dropwise via syringe. After 10 min the aldehyde (ca 7 g) in 59 mL THF was added dropwise via syringe. After 30 min, the mixture was added to 100 mL of water and was extracted with ether (100 mL). The ether layer was washed with sodium hydrogen phosphate (100 mL), dried, filtered, and concentrated in vacuo. This reaction was repeated on a second portion (8.5 g) of nitroketone, and the combined, crude product was chromatographed on 1 kg of silica gel (mplc) with 3:1 hexane/EtOAc to give 10.06 g (48% overall yield) pure diketo-olefin 6; NMR (60 MHz) 6.65 (dd, 1H; J=16,7 Hz), 6.0 (d, 1H, J=16 Hz), 3.55 (s,3H).

F. Bromo Diketo-olefin 7

To a solution of diketone 6 (5.04 g, 144 mmol) in 186 mL methylene chloride, stirred at rt, was added 1 equiv of bromine (as a ca 10% solution in carbon tetrachloride) dropwise via syringe. After the addition was complete, the mixture was concentrated in vacuo to an oil, which was then dissolved in 35 mL dry pyridine and heated in a 95° C. oil bath for 1 hr. The reaction mixture was cooled to rt and extracted from 200 mL 1N HCl with methylene chloride (3×200 mL). The combined extracts were filtered and concentrated in vacuo. The reaction was repeated twice on a 4.5 g scale. The combined, crude product was chromatographed on 1 kg of silica gel (mplc) with 3:1 hexane/EtOAc to give 14.55 g (84% overall yield) of pure 7: $^1$H NMR (60 MHz) 6.95 (d, 1H; J=9 Hz), 3.6 (s,3H).

G. Yne-diol 8

To a stirred suspension of sodium borohydride (1.15 g) in 382 mL dry methanol, at −10° C. under argon, was added a solution of bromo diketone 7 (14.55 g, 33.83 mmol) in 114 mL dry methanol, slowly via syringe. After 30 min, the reaction was quenched with 1N HCl. The mixture was extracted with methylene chloride to give, after concentration in vacuo, 14.886 g crude diol-olefin, which was used without purification in the next reaction.

To a solution of the crude diol-olefin (5.0 g, from the previous step) in 125 mL of 9:1 DMSO/methanol, stirred at rt under argon, was added 100 mL of a 9:1 (v/v) mixture of DMSO and 25% methanolic NaOMe (4.41N NaOMe in methanol). The dark purple solution was stirred overnight at rt. The reaction mixture was then extracted from 1N HCl with EtOAc; the combined organic layers were dried, filtered, and concentrated in vacuo. To the resulting concentrate was added 500 mL of methanol followed by 10 mL of boron trifluoride etherate. After refluxing 10 min on the steam bath, the solution was concentrated in vacuo to remove most of the methanol. Extraction of the concentrate from 1N sodium bicarbonate with methylene chloride gave, after concentration of the combined organic layers, crude diol 8. Two more runs of this reaction (on a 5 g and a 4 g scale) were performed; the combined, crude product from all three runs was chromatographed on 1 kg of silica gel (mplc) with 1.5:1 hexane/EtOAc; eluting first (Rf=0.27, 2:1 hexane/EtOAc) was 3.12 g of the 9 yne-diol: C-13 NMR (22.5 MHz) 174.3, 88.7, 81.8, 73.4, 62.6, 52.7, 51.4, 38.2, 34.0, 33.7, 33.2, 31.5, 30.5, 29.4, 28.9, 27.9, 27.5, 24.9, 22.6, 14.0 ppm; eluting next (Rf=0.22, same solvent) was 7.2 g of the 9 diol: C-13 NMR (22.5 MHz) 174.3, 88.2, 81.9, 78.0, 62.3, 55.0, 51.4, 38.0, 34.8, 33.9 (2C), 33.0, 31.4, 30.6, 29.3, 28.8, 27.2, 24.9 (2C), 22.4, 13.9 ppm. The overall yield of the isomeric yne-diols (=cpd 8) was thus 87% yield. It should be noted that both fractions above are mixtures of two diastereomers isomeric at C-15; since all four isomers oxidize to the desired prostaglandin analogue in the next step, it is not necessary to separate them.

H. 11-Deoxy-13,14-didehydro-15-oxo PGE$_1$

A mixture of yne-diol 8 (1.174 g), methanol (17 mL), and 1N sodium hydroxide (10 mL) was stirred at rt overnight. The mixture was then concentrated in vacuo to give the free acid in nearly quantitative yield; this material was used in the next reaction without further purification.

A portion of the free acid from above (0.854 g) was dissolved in acetone (26 mL) and cooled to $-10°$ C. with efficient stirring (mechanical stir). Standard Jones' reagent was added dropwise until the orange color persisted. The reaction was stirred for an additional 10 min and then was quenched with isopropanol. The mixture was filtered through fluted filter paper, and the green salts were washed well with acetone; the combined effluents were concentrated in vacuo and then were extracted from 1N HCl and EtOAc. The combined organic layers were dried, filtered, and concentrated in vacuo to give 761 mg crude product. Purification by PTLC (four 2000$\mu$ silica gel plates, developed twice with 60:20:0.5 cyclohexane/THF/formic acid) gave 0.556 g (65% yield) of pure 11-deoxy-13,14-didehydro-15 oxo-PGE$_1$: C-13 NMR (22.5 MHz) 216.6, 188.0, 179.5, 93.9, 81.7, 54.6, 45.4, 37.1, 33.9, 33.3, 31.1, 29.2, 28.8, 28.6, 27.4, 26.6, 24.6, 23.8, 22.3, 13.8 ppm.

The 11-hydroxy prostaglandin analogues of the present invention can be prepared from the corresponding natural prostaglandin, or by total synthesis.

For example, 13,14-didehydro PGF$_2$ can be prepared either by total synthesis (see Fried et al., J. Med. Chem. 16, 429 (1973) incorporated herein by reference, or by chemical modification of the natural prostaglandin PGF$_2$ (see U.S. Pat. No. 4,029,681, issued June 14, 1977 to Smith, incorporated herein by reference).

EXAMPLE II

Preparation of 13,14-didehydro-15-oxo-PGF$_{2\alpha}$ from 13,14-didehydro PGF$_{2\alpha}$ To a solution of 18 mg of 13,14-didehydro-PGF$_{2\alpha}$, stirred at 25° C. under argon, was added 50 mg imidazole and 50 mg t-butyldimethyl silyl chloride. After stirring 18 hr. at rt, the reaction mixture was extracted with Et$_2$O from 1N NaHCO$_3$. The ether layers were combined, dried, and concentrated under vacuum to give crude triether, which was purified by PTLC (10:1 hexane/EtOAc) to give 25 mg of trisilylether.

The triether was dissolved in 1 ml THF and cooled to 0° C. under argon. A 35 uL portion of tetrabutyl ammonium fluoride was added, and the mixture was stored at 0° C. for 48 hr. The reaction mixture was then chromatographed by PTLC to give 6 mg of 13,14-didehydro PGF$_{2\alpha}$-9,11-di(t-butyldimethylsilyl)ether, along with 6.5 mg 13,14-didehydro PGF$_{2\alpha}$ and other partially deprotected starting materials.

The disilyl ether (6 mg, as isolated above) was oxidized with pyridinium chlorochromate by the usual procedure to give, after PTLC on silica gel (7:1 hexane/EtOAc) 5.5 mg of 13,14-didehydro-15-oxo-PGF$_{2\alpha}$ methyl ester disilyl ester (IR (neat): 2200(s), 1730, 1665 cm$^{-1}$). A second run of this reaction produced 10.4 mg pure ynone product. That sample was dissolved in 2 ml of 3:1:1 HOAc/THF/H$_2$O and stirred at rt for 9 days. The sample was then concentrated in vacuo and purified by PTLC to give 4.2 mg pure 13,14-didehydro-15-keto PGF$_{2\alpha}$ methyl ester.

The corresponding E series compounds (e.g. 13,14-didehydro-15-keto PGE$_2$) are also prepared from 13,14-didehydro-15-keto PGF$_2$ by methods known in the art. See, for example, Fried et al., J. Med. Chem. 16, 429 (1973), incorporated herein by reference.

The 13,14-didehydro-15-oxo analogue of PGI$_2$ can be prepared using techniques similar to those disclosed by Sih, J. Org. Chem. 47, 4311 (1982) and by reference 6 cited therein, all of which are incorporated herein by reference.

A number of the 13,14-didehydro-15-oxo-prostaglandin analogues have been tested for cytoprotective activity in rats. In this test, Sprague-Dawley rats were fasted for 24 hours prior to the pretreatment. The pretreatment was oral administration of a 5 mg per kg body weight dose of the prostaglandin analogue in 2.5 mL of a vehicle consisting of Tween 80 (polyoxyethylene (20) sorbitan mono-oleate) (0.75%) and the balance water. The control animals were given 2.5 ml of the vehicle, without prostaglandin analogue. A half hour later after the pretreatment, absolute ethanol was administered orally to the animals, in a dose of 10 mL per kg body weight. One hour later the animals were sacrificed, their stomachs dissected out, opened along the greater curvature and the mucosa examined for lesions. The average lesion length is expressed as percentage of the average lesion length found in the stomach mucosa of control animals.

Importantly, this test measures the active cytoprotective properties of the prostaglandin analogues, independent of the gastric secretion inhibition that these compounds may or may not show. The test is discussed more fully by Robert et al., Gastroenterology 77 (1979) 433, incorporated herein by reference.

The prostaglandin analogues are identified by the name of the natural prostaglandin with which they share a common basic structure, and by identification of the structural variables, the more important of which are the nature of the C$_{13}$–C$_{14}$ bond (triple, cis-double, trans-double or single) and the substituent(s) at the 15 position (oxo, hydroxy or methyl, hydroxy).

| Test No. | Type PG | 7 | 13–14 | 15 | Other | Dose mg/kg | Cytoprotection % |
|---|---|---|---|---|---|---|---|
| 1* | PGE$_1$ | | triple | oxo | (a) (d) | 1 | 81 |
| 2* | PGE$_1$ | | triple | oxo | (a) (d) | 5 | 96 |
| 3* | PGE$_1$ | | triple | oxo | (a) (d) | 0.5 | 39 |
| 4* | PGE$_1$ | | triple | oxo | (a) (d) | 3 | 78 |
| 5 | PGE$_1$ | | trans | oxo | (a) (d) | 0.5 | $-22^{(b)}$ |
| 6 | PGE$_1$ | | trans | oxo | (a) (d) | 3 | 52 |
| 7 | PGF$_{2\alpha}^{(c)}$ | | trans | OH | (a) | 0.001 | $-19^{(b)}$ |
| 8 | PGF$_{2\alpha}^{(c)}$ | | trans | OH | (a) | 0.01 | 1.7 |
| 9 | PGF$_{2\alpha}^{(c)}$ | | trans | OH | (a) | 0.1 | $-17^{(b)}$ |
| 10 | PGF$_{2\alpha}^{(c)}$ | | trans | OH | (a) | 0.5 | 82 |
| 11* | PGF$_{2\alpha}$ | | triple | oxo | (a) | 0.001 | 6 |
| 12* | PGF$_{2\alpha}$ | | triple | oxo | (a) | 0.01 | 23 |
| 13* | PGF$_{2\alpha}$ | | triple | oxo | (a) | 0.1 | 50 |
| 14* | PGF$_{2\alpha}$ | | triple | oxo | (a) | 0.5 | 98 |

(a) methyl ester
(b) lesions worse than control
(c) natural prostaglandin
(d) 11-deoxy
*a compound of the present invention The 13,14-didehydro-15-oxo analogue of PGF$_{2\alpha}$ (tests nos. 11–14) is a much more potent cytoprotective agent than PGF$_{2\alpha}$ itself (tests nos. 7–10).

In general, the combination of a C$_{13}$–C$_{14}$ triple bond and a 15-oxo substituent results in very good cytoprotective properties of the compound.

One of the most important side-effects of prostaglandins and prostaglandin analogues is their diarrheogenic effect. An assay was developed by Robert to test the diarrheogenic properties of prostaglandins and prostaglandin analogues. The test quantitatively determines the amount of "enteropooling", i.e. the accumulation of fluid into the small intestine. A full description of the assay is found in A. Robert, *Advances in Prostaglandin and Thromboxane Research* (1975) p. 947, Raven Press, New York, the disclosures of which are incorporated herein by reference.

The diarrheogenic effect of the 11-deoxy-13,14-didehydro-15-oxo-PGE$_1$ analogue (hereinafter referred to as compound 1) was determined and compared with those of PGE$_2$ (natural prostaglandin), 15(R),15-methyl-PGE$_2$ and 16,16-dimethyl-PGE$_2$. The latter two compounds have been developed by the Upjohn Company for the treatment of gastric ulcers (see Nelson et al., C&EN, Aug. 16, 1982, pp. 30–44).

|  | Enteropooling Dose mg/kg | ED$_{50}$ Cytoprotection ug/kg | TI[a] |
|---|---|---|---|
| Compound 1 | 25 | 100 | 250 |
| PGE$_2$ | 0.750 | 25 | 30 |
| 15(R)-15-methyl PGE$_2$ | 0.005 | 0.05–0.2 | 25–100 |
| 16,16-dimethyl PGE$_2$ | 0.0005 | 0.05 | 10 |

[a]therapeutic index, defined as $\frac{ED_{50} \text{ Enteropooling}}{ED_{50} \text{ Cytoprotection}}$ The results show that compound 1, a prostaglandin analogue within the scope of the present invention, has a very low diarrheogenic effect as compared to PGE$_2$ and PGE$_2$ analogues which were specifically developed for the treatment of gastric ulcers. As a result, the therapeutic index of compound 1 is significantly higher than those of any of the other compounds. Another important side effect of natural prostaglandins and prostaglandin analogues is their abortificative effect. Compound 1 was tested for this effect as follows. The compound was administered orally at a dose of 25 mg/kg (the ED$_{50}$ for enteropooling and 250 times the ED$_{50}$ for cytoprotection) to pregnant quinea pigs on days 43 and 44 of gestation. A total of 6 animals were treated this way; in none of the animals did the dose of compound 1 induce abortion.

The smooth muscle contraction potency of compound 1 was tested in the rat fundic strip assay, described by W. L. M. Perry in "Pharmacological Experiments on Isolated Preparations," 2nd ed. (1970), pp. 88–89, Churchill L. Livingstone, publisher.

The EC$_{50}$ for smooth muscle contraction for compound 1 is $5 \times 10^{-6}$M, which is two orders of magnitude higher than the EC$_{50}$ values for PGF$_{2\alpha}$, and PGE$_1$ and three orders of magnitude higher than the value for PGE$_2$.

Hence, compound 1 is a potent cytoprotective agent, and has a low potency for diarrhea, abortion and smooth muscle contraction.

The above tests are repeated with the 13,14-didehydro-15-oxo analogues of PGF$_3$, PGE$_1$ and PGE$_2$; the 11-deoxy-13,14-didehydro-15-oxo analogues of PGF$_{2\alpha}$, and PGE$_2$; and the 6a-carba-13,14-didehydro-15-oxo analogue of PGI$_2$. Substantially the same results are obtained.

Another aspect of this invention is a pharmaceutical composition comprising a safe and effective amount of a prostaglandin analogue of the present invention, or a pharmaceutically acceptable salt or ester thereof, and a pharmaceutical carrier.

By "safe and effective amount" herein is meant an amount sufficient to produce a significant level of cytoprotection, but low enough so as not to create serious side effects. The acceptability of a certain level of side effect depends on factors like the general condition of the patient, the seriousness of the condition to be treated, the age of the patient, special conditions (like pregnancy) and the like; the determination of what constitutes a safe level will ultimately have to be made by the physician treating the patient and on a case by case basis. In general, a safe and effective amount of the prostaglandin analogues of the present invention may range from about 0.001 mg/kg to about 25 mg/kg. A safe and effective amount in a unit dosage form ranges from about 0.07 mg to about 2 g, but preferably is from about 0.2 mg to about 1 g.

The choice of the pharmaceutical carrier to be used in conjunction with the prostaglandin analogues of the present invention is basically determined by the way the prostaglandin analogue is to be administered. If the compound is to be injected, the preferred pharmaceutical carrier is distilled, nonpyrogenic water, the pH of which has been adjusted to about 7.4. However, the preferred mode of administering the prostaglandin analogues of the present invention is orally, and the preferred unit dosage form is therefore tablets, capsules, and the like. Pharmaceutical carriers suitable for the preparation of unit dosage forms for oral administration are well known in the art. Their selection will depend on secondary considerations like taste, cost, shelf stability, which are not critical for the purposes of the present invention, and may be made without difficulty by a person skilled in the art. The amount of pharmaceutical carrier may range from about 50 mg to about 2 g.

This invention further provides a method for treating or preventing gastric inflammatory diseases in humans and lower animals at risk to such disease, comprising the step of administering to such human or lower animal a safe and effective amount of a prostaglandin analogue of the present invention. Oral administration is the preferred mode of administration.

EXAMPLE III

Capsules are prepared by conventional methods, comprised as follows

| Ingredient | mg per capsule |
|---|---|
| 13,14-didehydro-15-oxo PGE$_1$ | 35 |
| starch | 500 |
| sodium lauryl sulfate | 29 |

The above capsules administered twice daily substantially reduce gastric ulceration in a patient weighing approximately 70 kilograms. Similar results are obtained with capsules comprising 13,14-didehydro-15-oxo-PGF$_{2\alpha}$ (20 mg); 13,14-didehydro-15-oxo-PGE$_2$ (5 mg); 11-deoxy-13,14-didehydro-15-oxo-PGE$_1$ (8 mg); and 6a-carba-13,14-didehydro-15-oxo-PGI$_2$ (10 mg).

EXAMPLE IV

Tablets are prepared by conventional methods, formulated as follows:

| Ingredient | mg per tablet |
|---|---|
| 13,14-didehydro-15-oxo-PGF$_{2\alpha}$ | 10 |
| lactose | 40 |
| starch | 250 |

| Ingredient | mg per tablet |
| --- | --- |
| magnesium stearate | 1 |

When administered orally four times daily, the above composition effectively reduces the incidence of gastric ulceration in patients suffering from arthritis who receive daily oral doses of 1000 mg aspirin.

Similar results are achieved with tablets formulated as above but replacing 13,14-didehydro-15-oxo-PGF$_2$ with 9-methoxy-13,14-didehydro-15-oxo-PGF$_{2\alpha}$ (200 mg); 13,14-didehydro-15-oxo-PGE$_1$ (methyl ester) (5 mg); 13,14-didehydro-15-oxo-PGE$_2$ (sodium salt) (18 mg); 11-deoxy-13,14-didehydro-15-oxo PGl$_2$ (potassium salt) (0.1 mg); and 2,2-dimethyl-13,14-didehydro-15-oxo-16-methyl-PGE$_2$ (0.5 mg).

What is claimed is:

1. The 13,14-didehydro-15-oxo-prostaglandin analogues of the formula:

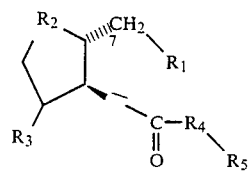

wherein R$_1$ is

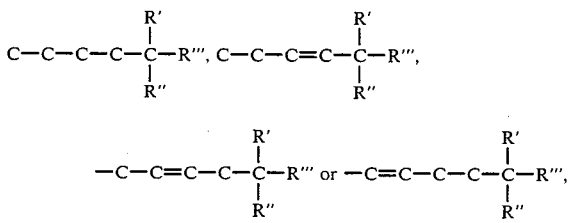

wherein
R' and R" are each independently H, CH$_3$, C$_2$H$_5$ or C$_3$H$_7$, and R''' is CH$_2$OH, or COOR$_6$;
R$_2$ is

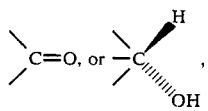

R$_3$ is hydrogen, hydroxyl, or hydroxymethyl, methylene, or R''''—O—, wherein R'''' is an alkyl having from 1 to 4 carbon atoms;
R$_4$ is

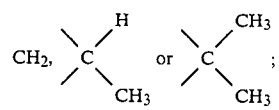

R$_5$ is C$_2$H$_5$; C$_3$H$_7$, C$_4$H$_9$ or C$_5$H$_{11}$; and
R$_6$ is
(a) hydrogen,
(b) alkyl or one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive,
(g) —(p—Ph)—CO—CH$_3$, wherein (p—Ph) is para-phenyl or inter-paraphenylene,
(h) —(p—Ph)—NH—CO—(p—Ph)—NH—CO—CH$_3$,
(i) —(p—Ph)—NH—CO—(p—Ph),
(j) —(p—Ph)—NH—CO—CH$_3$,
(k) —(p—Ph)—NH—CO—NH$_2$,
(l) —(p—Ph)—CH=N—NH—CO—NH$_2$,
(m) $\beta$-naphthyl,
(n) —CH$_2$—CO—R$_7$, wherein R$_7$ is phenyl, p-bromophenyl, p-biphenylyl, p-nitrophenyl, p-benzamidophenyl, or 2-naphthyl, or
(o) a pharmaceutically acceptable cation.

2. The prostaglandin analogues of claim 1 wherein R$_4$ is CH$_2$ and R$_5$ is C$_4$H$_9$.

3. The prostaglandin analogues of claim 1 wherein R$_3$ is hydrogen.

4. The prostaglandin analogues of claim 1 wherein R$_2$ is >C=O.

5. The prostaglandin analogues of claim 1 wherein R$_1$ is C$_5$H$_{10}$COOR$_6$.

6. The prostaglandin analogues of claim 1 wherein R$_1$ is —C—C=C$_3$H$_6$COOR$_6$.

7. Prostaglandin analogues of claim 1 of the formula:

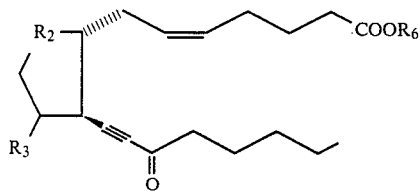

wherein R$_2$ is

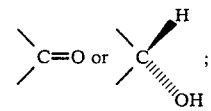

and R$_3$ is hydrogen, hydroxyl, or hydroxymethyl.

8. Prostaglandin analogues of claim 1 of the formula:

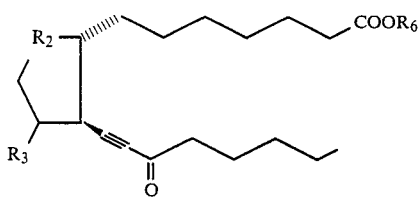

wherein R$_2$ is

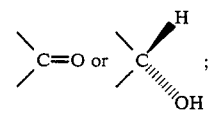

and R$_3$ is hydrogen, hydroxyl, or hydroxymethyl.

9. The 13,14-didehydro-15-oxo-PGF$_{2\alpha}$ analogue, and pharmaceutically acceptable salts and esters according to claim 1 thereof.

10. The 13,14-didehydro-15-oxo-PGE$_2$ analogue, and pharmaceutically acceptable salts and esters according to claim 1 thereof.

11. The 13,14-didehydro-15-oxo-PGE$_1$ analogue, and pharmaceutically acceptable salts and esters according to claim 1 thereof.

12. The 11-deoxy-13,14-didehydro-15-oxo-PGF$_{2\alpha}$ analogue, and pharmaceutically acceptable salts and esters according to claim 1 thereof.

13. The 11-deoxy-13,14-didehydro-15-oxo-PGE$_{2\alpha}$ analogue, and pharmaceutically acceptable salts and esters according to claim 1 thereof.

14. The 11-deoxy-13,14-didehydro-15-oxo-PGE$_1$ analogue, and pharmaceutically acceptable salts and esters according to claim 1 thereof.

15. A pharmaceutical composition in unit dosage form for treating and preventing gastric inflammatory diseases, comprising:
    (a) a safe and effective amount of the prostaglandin analogue of claim 1; and
    (b) a pharmaceutical carrier.

16. A pharmaceutical composition in unit dosage form for treating and preventing gastric inflammatory diseases, comprising:
    (a) a safe and effective amount of the prostaglandin analogue of claim 7; and
    (b) a pharmaceutical carrier.

17. A pharmaceutical composition in unit dosage form for treating and preventing gastric inflammatory diseases, comprising:
    (a) a safe and effective amount of the prostaglandin analogue of claim 8; and
    (b) a pharmaceutical carrier.

18. A pharmaceutical composition in unit dosage form for treating and preventing gastric inflammatory diseases, comprising:
    (a) a safe and effective amount of the prostaglandin analogue of claim 9; and
    (b) a pharmaceutical carrier.

19. A pharmaceutical composition in unit dosage form for treating and preventing gastric inflammatory diseases, comprising:
    (a) a safe and effective amount of the prostaglandin analogue of claim 10; and
    (b) a pharmaceutical carrier.

20. A pharmaceutical composition in unit dosage form for treating and preventing gastric inflammatory diseases, comprising:
    (a) a safe and effective amount of the prostaglandin analogue of claim 11; and
    (b) a pharmaceutical carrier;

21. A pharmaceutical composition in unit dosage form for treating and preventing gastric inflammatory diseases, comprising:
    (a) a safe and effective amount of the prostaglandin analogue of claim 12; and
    (b) a pharmaceutical carrier.

22. A pharmaceutical composition in unit dosage form for treating and preventing gastric inflammatory diseases, comprising:
    (a) a safe and effective amount of the prostaglandin analogue of claim 13; and
    (b) a pharmaceutical carrier.

23. A pharmaceutical composition in unit dosage form for treating and preventing gastric inflammatory diseases, comprising:
    (a) a safe and effective amount of the prostaglandin analogue of claim 14; and
    (b) a pharmaceutical carrier.

24. A method for treating or preventing gastric inflammatory disease in humans or lower animals at risk to said disease, comprising the step of administering to such human or lower animal a safe and effective amount of the prostaglandin analogue of claim 1.

25. A method for treating or preventing gastric inflammatory disease in humans or lower animals at risk to said disease, comprising the step of administering to such human or lower animal a safe and effective amount of the prostaglandin analogue of claim 7.

26. A method for treating or preventing gastric inflammatory disease in humans or lower animals at risk to such disease, comprising the step of administering to such human or lower animal a safer and effective amount of the prostaglandin analogue of claim 8.

27. A method for treating or preventing gastric inflammatory disease in humans or lower animals at risk to such disease, comprising the step of administering to such human or lower animal a safe and effective amount of the prostaglandin analogue of claim 9.

28. A method for treating or preventing gastric inflammatory disease in humans or lower animals at risk to such disease, comprising the step of administering to such human or lower animal a safe and effective amount of the prostaglandin analogue of claim 10.

29. A method for treating or preventing gastric inflammatory disease in humans or lower animals at risk to such disease, comprising the step of administering to such human or lower animal a safe and effective amount of the prostaglandin analogue of claim 1.

30. A method for treating or preventing gastric inflammatory disease in humans or lower animals at risk to such disease, comprising the step of administering to such human or lower animal a safe and effective amount of the prostaglandin analogue of claim 12.

31. A method for treating or preventing gastric inflammatory disease in humans or lower animals at risk to such disease, comprising the step of administering to such human or lower animal a safe and effective amount of the prostaglandin analogue of claim 13.

32. A method for treating or preventing gastric inflammatory disease in humans or lower animals at risk to such disease, comprising the step of administering to such human or lower animal a safe and effective amount of the prostaglandin analogue of claim 14.

* * * * *